(12) United States Patent
Shimmura et al.

(10) Patent No.: US 6,514,239 B2
(45) Date of Patent: Feb. 4, 2003

(54) MEDICAL INSTRUMENT HOLDING APPARATUS

(75) Inventors: Toru Shimmura, Hachioji (JP); Koji Yasunaga, Hino (JP); Masaki Takayama, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 127 days.

(21) Appl. No.: 09/811,723

(22) Filed: Mar. 19, 2001

(65) Prior Publication Data

US 2001/0027313 A1 Oct. 4, 2001

(30) Foreign Application Priority Data

Mar. 22, 2000 (JP) ........................................ 2000-080874

(51) Int. Cl.$^7$ .............................................. A61B 19/00
(52) U.S. Cl. ............................ 606/1; 606/130; 600/427
(58) Field of Search ........................... 606/1, 130, 427, 606/429, 471, 345, 407, 445, 437, 459; 604/22

(56) References Cited

U.S. PATENT DOCUMENTS

| | | | | |
|---|---|---|---|---|
| 5,017,139 A | * | 5/1991 | Mushabac | 433/108 |
| 5,170,790 A | | 12/1992 | Lacoste et al. | 600/437 |
| 5,480,212 A | * | 1/1996 | Marconet | 248/124.1 |
| 5,697,939 A | * | 12/1997 | Kubota et al. | 606/130 |
| 5,812,301 A | * | 9/1998 | Nakamura | 248/123.11 |
| 5,907,387 A | * | 5/1999 | Schwaegerle | 351/200 |
| 6,085,749 A | * | 7/2000 | Wardle et al. | 128/845 |
| 6,434,416 B1 | * | 8/2002 | Mizoguchi et al. | 600/427 |
| 2002/0064048 A1 | * | 5/2002 | Sander | 362/401 |
| 2002/0074472 A1 | * | 6/2002 | Gaida et al. | 600/429 |

FOREIGN PATENT DOCUMENTS

| | | | | |
|---|---|---|---|---|
| JP | 7-289563 | | 11/1995 | |
| JP | 8-52158 | | 2/1996 | |
| JP | 2001-137258 | * | 5/2001 | A61B/19/00 |

* cited by examiner

Primary Examiner—Hieu T. Vo
(74) Attorney, Agent, or Firm—Frishauf, Holtz, Goodman & Chick, P.C.

(57) ABSTRACT

A medical instrument holding apparatus comprises a support arm supported such that it is rotatable about a first axis of rotation, a first arm supported such that it is rotatable about a second axis of rotation, a second arm supported such that it is rotatable about a third axis of rotation, and a third arm supported such that it is rotatable about a fourth axis of rotation. This apparatus further comprises first, second, third and fourth locks for locking the support arm, the first arm, the second arm and the third arm about the first, second, third and fourth axes of rotation, respectively, and for releasing the locked states of the arms. This apparatus can select control for causing predetermined three of the first, second, third and fourth locks to execute a locking operation, or control for causing all the locks to execute the locking operation.

21 Claims, 7 Drawing Sheets

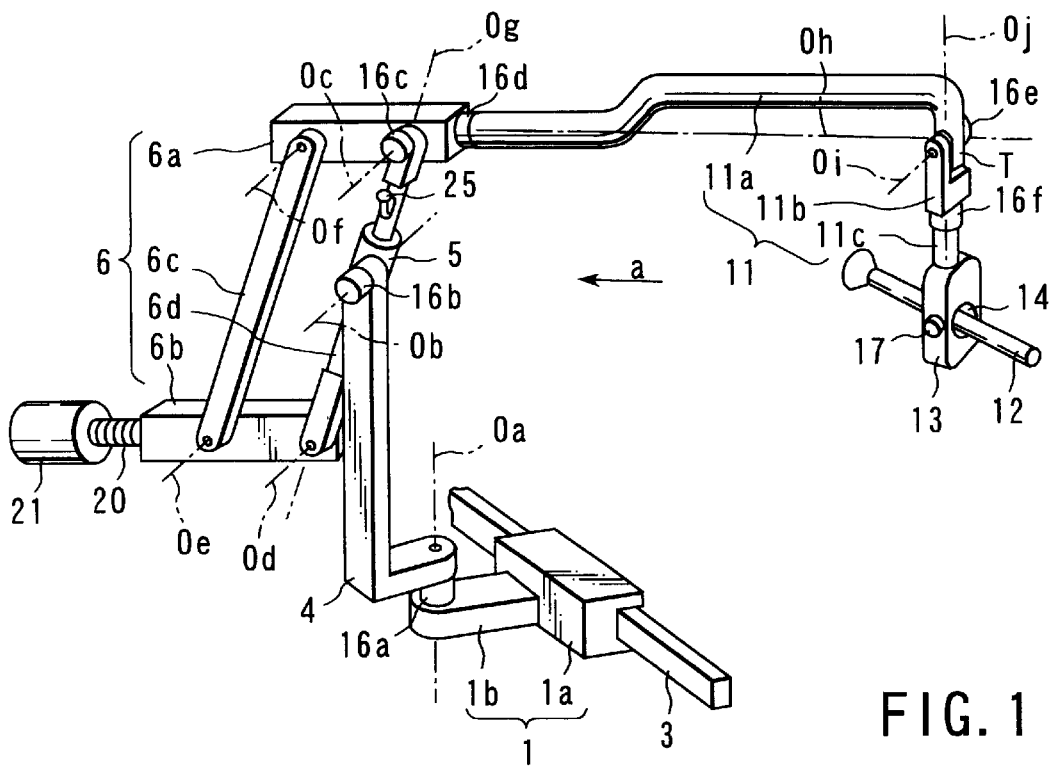
FIG. 1
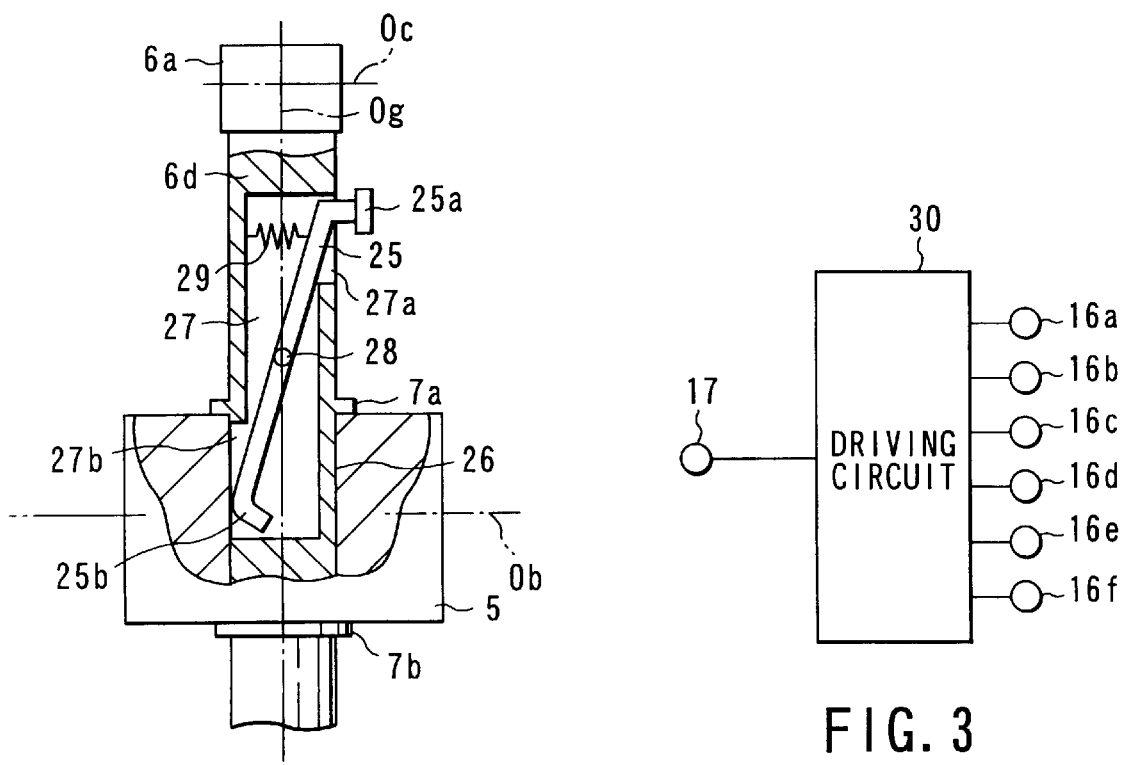
FIG. 2
FIG. 3

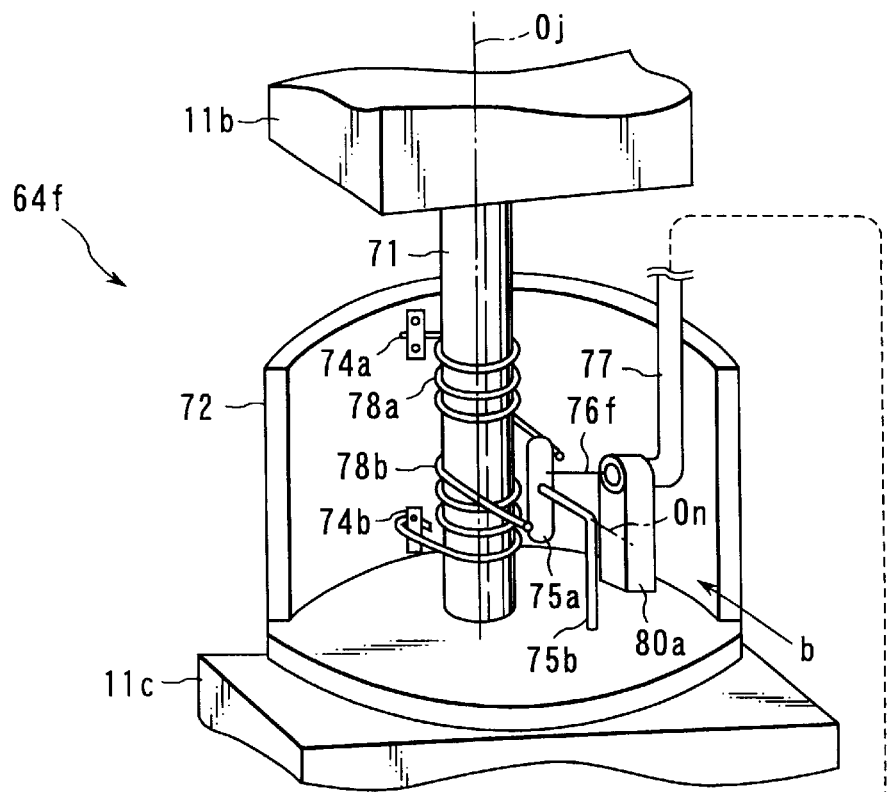
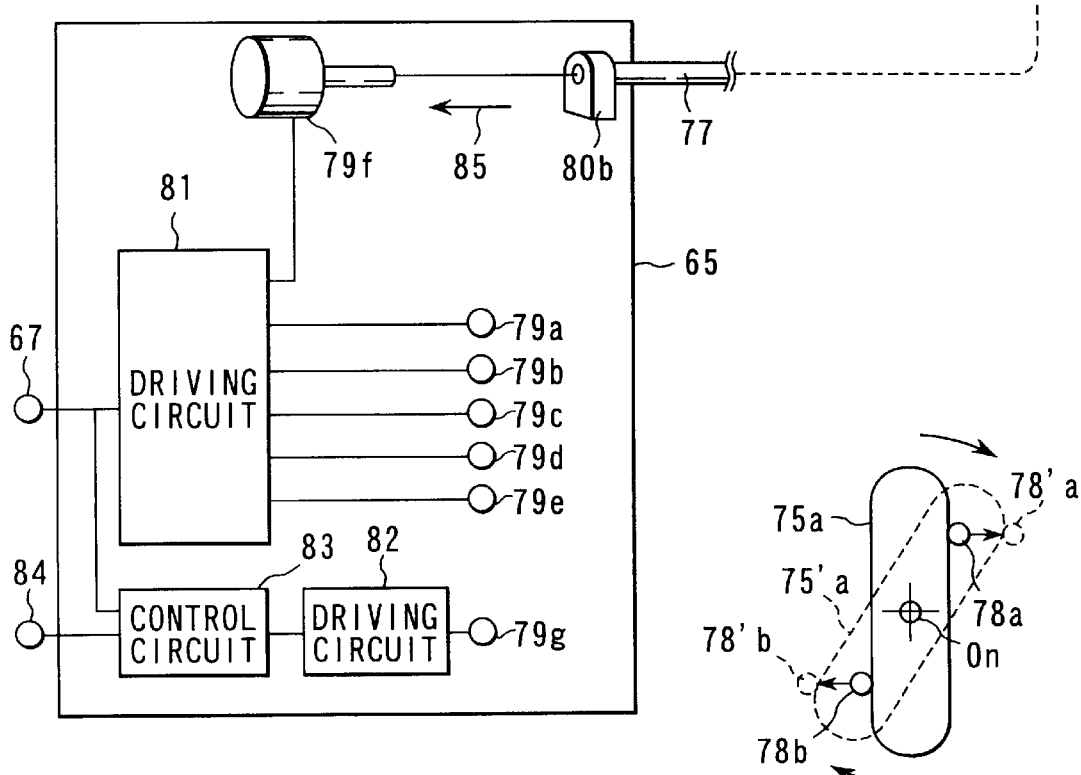
FIG. 11
FIG. 12

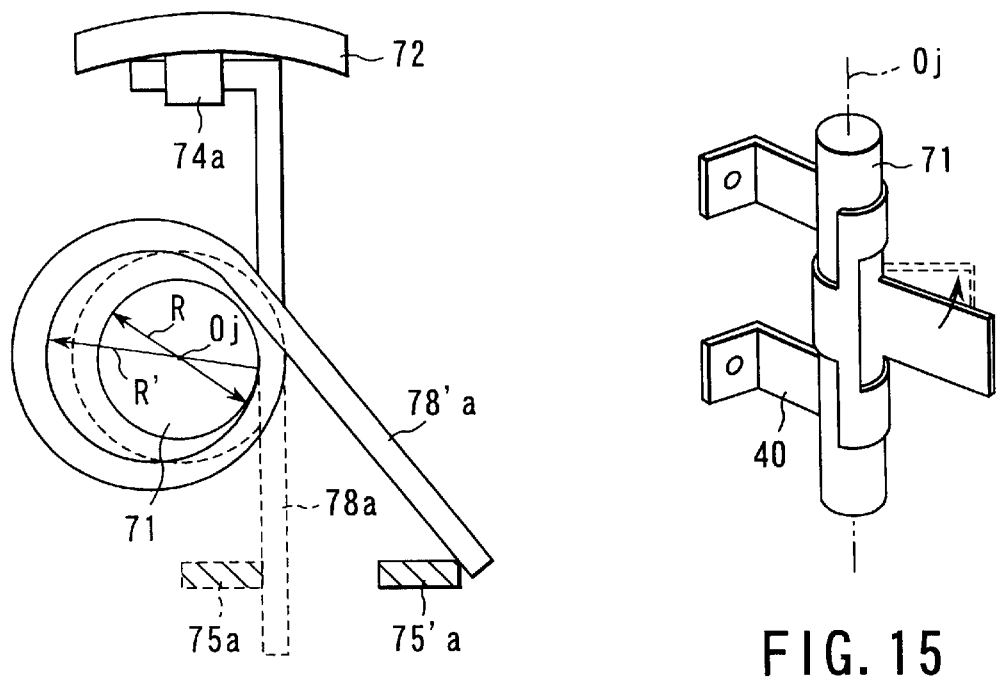
FIG. 13
FIG. 15
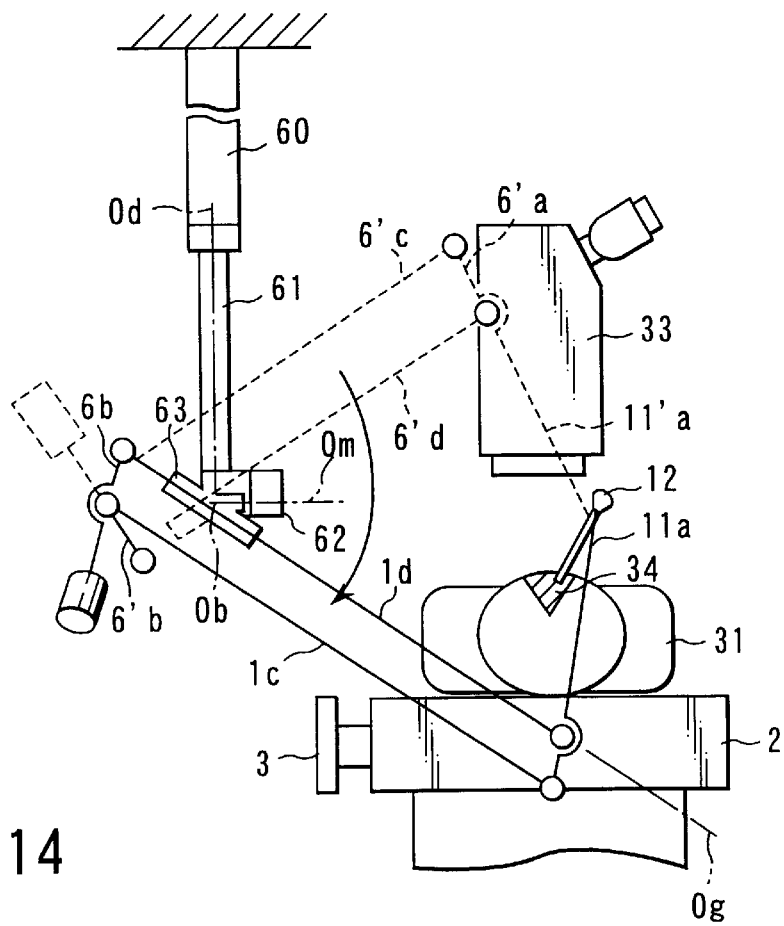
FIG. 14

MEDICAL INSTRUMENT HOLDING APPARATUS

CROSS-REFERENCE TO RELATED APPLICATIONS

This application is based upon and claims the benefit of priority from the prior Japanese Patent Application No. 2000-080874, filed Mar. 22, 2000, the entire contents of which are incorporated herein by reference.

BACKGROUND OF THE INVENTION

The present invention relates to a medical instrument holding apparatus for holding a medical instrument such as an endoscope or a treatment tool, etc. when executing a treatment using a microscope.

In recent years, micro-surgery using a surgical microscope is often being executed in cranial nerve surgery. The observation range of the surgical microscope is limited to a range within which observation is executed through an incised portion of a braincase. In other words, there is an area (blind spot) that cannot be observed by the surgical microscope. When observing such a blind spot, an endoscope is used.

The endoscope is used while it is fixed and supported by a medical instrument holding apparatus having a plurality of arm joints. While observing an image through the endoscope, a treatment tool is inserted into a to-be-treated portion in a braincase, thereby executing an operation.

Since, in the braincase, various kinds of important fine tissue are intertwined in a complicated and delicate manner, the aforementioned holding apparatus is required to enable the endoscope to move smoothly and delicately without injuring the tissue, or enable it to be fixed in an accurate portion.

Jpn. Pat. Appln. KOKAI Publication No. 7-289563 discloses a medical instrument holding apparatus, which has a counterbalance mechanism for offsetting the weight of a medical instrument such as an endoscope, thereby enabling a held medical instrument to move smoothly.

Further, Jpn. Pat. Appln. KOKAI Publication No. 8-52158 discloses a medical instrument holding apparatus, in which a pair of spherical surface elements are provided at the joint of each arm section, thereby enabling the arm section to crawl around.

Since, in cranial nerve surgery, a treatment is executed while observing a surgical microscope as aforementioned, it is important that the arm section of the medical instrument holding apparatus does not interrupt the field of vision or the operation of the instrument by the doctor. Moreover, there is a case where the endoscope is inserted into, for example, a tumor in the pituitary gland of a patient through the nose. In this case, the arm section must be positioned above the patient.

In the case of the medical instrument holding apparatus disclosed in Jpn. Pat. Appln. KOKAI Publication No. 7-289563, a medical instrument held by it is enabled to be tilted about three axes of rotation, i.e. tilted with three degrees of freedom, and to be three-dimensionally positioned with three degrees of freedom by pivoting or rotating operations about three axes of rotation.

Therefore, in this case, once fixing the installation position of the holding apparatus and the position of the distal end of the endoscope, the arm section of the holding apparatus situated between the installation position and the endoscope is fixed in position and cannot be moved to an appropriate position that matches the conditions of a surgical operation. Furthermore, it is possible that the arm section interrupts the field of vision of the surgical microscope or the doctor's operation of the instrument.

On the other hand, in the medical instrument holding apparatus disclosed in Jpn. Pat. Appln. KOKAI Publication No. 8-52158, the arm section can be situated in a most appropriate position since a pair of spherical surface elements are provided at the joint of each arm section.

However, this apparatus does not have any balancing function for offsetting the weight of an endoscope, and therefore the endoscope cannot easily be moved.

BRIEF SUMMARY OF THE INVENTION

The present invention has been developed in light of the above-described circumstances, and aims to provide a medical instrument holding apparatus applicable to various types of medical instruments, and capable of selecting the holding position and angle of each medical instrument without interrupting the field of vision of its surgical microscope and the operation of the instrument.

The present invention also aims to provide a compact and lightweight medical instrument holding apparatus.

According to an aspect of the invention, there is provided a medical instrument holding apparatus comprising:

an installation section to be supported by a member in an operation room;

a support arm supported by the installation section such that the support arm is rotatable about a first axis of rotation;

a first arm supported by the support arm such that the first arm is rotatable about a second axis of rotation perpendicular to the first axis of rotation;

a second arm supported by the first arm such that the second arm is rotatable about a third axis of rotation perpendicular to the second axis of rotation;

a third arm supported by the second arm such that the third arm is rotatable about a fourth axis of rotation perpendicular to the third axis of rotation;

a holding section tilting/rotating mechanism supported by a front end portion of the third arm;

a medical instrument holding section supported by the holding section tilting/rotating mechanism such that the medical instrument holding section is tiltable and rotatable, the medical instrument holding section being designed to hold a medical instrument;

first, second, third and fourth locking units for locking the support arm, the first arm, the second arm and the third arm rotating about the first axis of rotation, the second axis of rotation, the third axis of rotation and the fourth axis of rotation, respectively, and for releasing locked states of the support arm, the first arm, the second arm and the third arm; and a control unit capable of controlling a selected one of the first, second, third and fourth locking units.

The holding apparatus constructed as above can easily select a medical-instrument-holding position appropriate to any surgical operation. When the holding apparatus has selected an operation for enabling the arms to be moved with three degrees of freedom, a medical instrument held by the holding section can be moved. After that, when all the first, second, third and fourth locking units have been released using selection means, the holding apparatus has four degrees of freedom, whereby the positions of the arms can be moved without changing the position of the holding section and the position of the front end of the medical instrument.

Preferably, the medical instrument holding apparatus has an operation switching unit for switching an operation of the control unit between control for causing predetermined three of the first, second, third and fourth locking units to execute a locking operation, and control for causing all the first, second, third and fourth locking units to execute a locking operation.

Accordingly, the positions of the arms can be easily moved without changing the position of the holding section and the position of the front end of the medical instrument.

According to another aspect of the invention, there is provided a medical instrument holding apparatus comprising:

an arm unit including a plurality of arm members supported such that the arm members are rotatable about their respective axes of rotation;

locking units for locking the respective arm members of the arm unit about their respective axes, and for releasing a locked state of the arm members, the locking units each having a support shaft arranged coaxially with a corresponding one of the axes, a coiled elastic member mounted on the support shaft, and a deforming unit for deforming and enlarging a diameter of the coiled elastic member, the diameter of the coiled elastic member being smaller than an outer diameter of the support shaft when the coiled elastic member is in a natural state; and a medical instrument holding section supported by one of the arm members for holding a medical instrument.

In this structure, the fastening force of each elastic member can stop a corresponding arm rotating about its axis. This structure enables the locking mechanism and hence the holding apparatus itself to be made compact and lightweight.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a schematic perspective view illustrating a medical instrument holding apparatus according to a first embodiment;

FIG. 2 is a longitudinal sectional view illustrating a pressing lever incorporated in the medical instrument holding apparatus of the first embodiment;

FIG. 3 is a view useful in explaining an electrical circuit incorporated in the medical instrument holding apparatus of the first embodiment;

FIG. 11 is a view useful in explaining a spring-tensioned locking mechanism, a solenoid box and its electrical circuit, which are incorporated in the medical instrument holding apparatus according to the third embodiment;

FIG. 12 is a view useful in explaining a rotatable block included in the locking mechanism of FIG. 11, when viewed in a direction indicated by arrow b in FIG. 11;

FIG. 13 is a view useful in explaining the deformation of a return spring included in the locking mechanism of FIG. 11;

FIG. 14 is a view useful in explaining a state of a surgical operation using the medical instrument holding apparatus of the third embodiment; and FIG. 15 is a perspective view illustrating a modification of the spring used in the locking mechanism.

Figure 4:
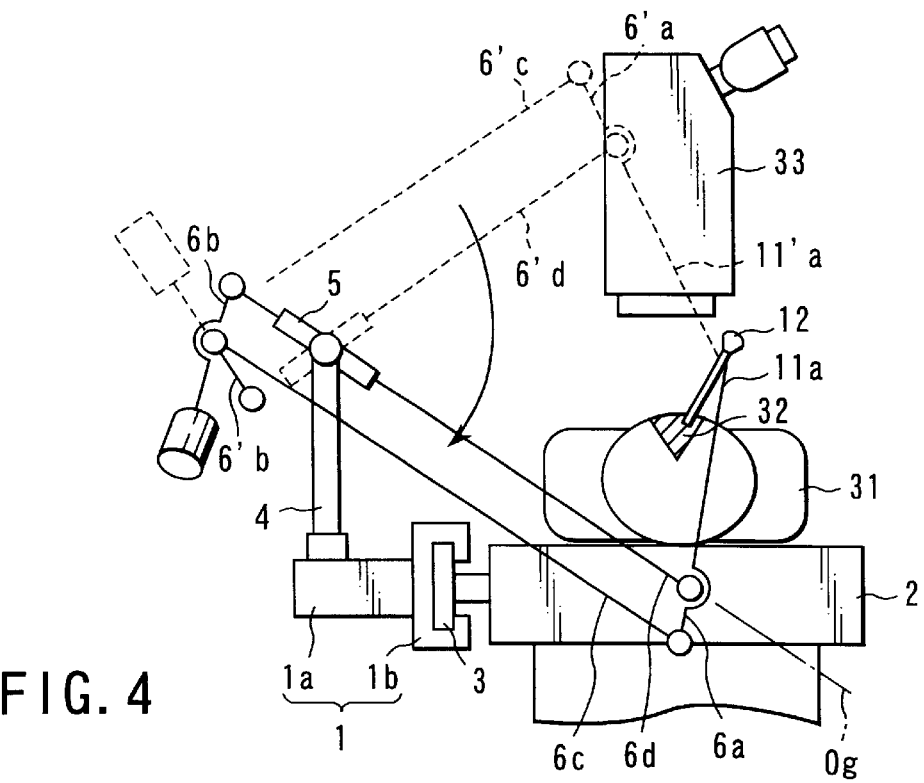
FIG. 4 is a view useful in explaining a state of a surgical operation using the medical instrument holding apparatus of the first embodiment.

DETAILED DESCRIPTION OF THE INVENTION (First Embodiment)

Referring first to FIGS. 1–6, a medical instrument holding apparatus according to a first embodiment will be described.

FIG. 1 schematically shows the medical instrument holding apparatus according to the first embodiment. In FIG. 1, reference numeral 1 denotes an installation section included in the apparatus. This section comprises an installation table 1a that can be fixed to a side rail 3 attached to a surgical bed 2 (see FIGS. 4 and 5), and a support table 1b laterally projecting from the installation table 1a. The installation table 1a is detachably and slidably engaged with the side rail 3, and fastened thereto by a fastening screw (not shown) in a position appropriate for surgery. FIG. 1 shows a state in which the installation section 1 is fixed.

One horizontal end portion of a crank-shaped support arm 4 is connected to the support table 1b of the installation section 1 such that it can pivot or rotate about an axis-of-rotation Oa (first axis of rotation) that extends vertically. The other end portion of the support arm 4 extends vertically upward in parallel with respect to the axis-of-rotation Oa, and can pivot or rotate about the axis-of-rotation Oa. The upper end of the other end portion of the support arm 4 supports an upper support member 5 as a first arm such that the member 5 can pivot or rotate about an axis-of-rotation Ob (second axis of rotation), which extends perpendicular to the axis-of-rotation Oa.

A first parallel crank link mechanism 6 as balancing means is coupled to the upper support member 5. The first parallel link mechanism 6 includes an arm 6d (second arm) extending through the upper support member 5 and coaxially supported by it, an arm 6a (third arm) having one end thereof connected to the upper end of the arm 6d, an arm 6b having one end thereof connected to the lower end of the arm 6d, and an arm 6c connecting the arm 6a to the arm 6b. The arms 6a and 6b are parallel to each other, while the arms 6c and 6d are also parallel to each other. The arms 6a and 6b are maintained in a parallel relationship to each other by the arms 6c and 6d, which can pivot or rotate about axes-of-rotation Oe and Of, Oc (fourth axis of rotation) and Od, respectively. Since thus, the arms 6a, 6b, 6c and 6d constitute a parallel link mechanism, the arm 6a is arranged to move in a vertical plane, kept parallel to the arm 6b.

Further, the upper support member 5 supports the arm 6d as the second arm such that the arm can rotate about an axis-of-rotation Og (third axis of rotation), which is perpendicular to the axes-of-rotation Ob, Oc and Od.

The front end of the arm 6a of the first parallel link mechanism 6 is connected to an arm 11a incorporating a link mechanism 11 as a holding section tilting mechanism.

The link mechanism 11 includes arms 11a, 11b and 11c. The arm 11a can pivot or rotate about an axis-of-rotation Oh perpendicular to the axes-of-rotation Oc-Of, and is supported by the arm 6a. The angled end of the arm 11a supports the arm 11b such that the arm 11b can pivot or rotate about an axis-of-rotation Oi perpendicular to the axis-of-rotation Oh. The arm 11b supports the arm 11c such that the arm 11c can pivot or rotate about an axis-of-rotation Oj, which passes through an intersection T between the axes-of-rotation Oh and Oi and is perpendicular to them.

The arm 11c of the link mechanism 11 has a holding section 13 that holds a rigid scope 12 as an auxiliary endoscope. The link mechanism 11 constitutes a holding section tilting mechanism that supports the holding section 13 such that the section 13 can tilt and rotate.

The holding section 13 has a holding hole 14 in which the rigid scope 12 is removably inserted. The holding section 13 includes a release switch 17 serving as first input means for releasing electromagnetic locks 16a–16f, which serve as locking means for locking respective movable sections.

The electromagnetic locks 16a–16f as means for braking their respective movable sections will be described. In FIG. 1, the electromagnetic lock 16a is provided on the support table 1b, and serves as first locking means capable of electrically locking the support arm 4 about the axis-of-rotation Oa relative to the support table 1b. The electromagnetic lock 16b is provided on an upper end portion of the support arm 4, and serves as second locking means capable of electrically locking the upper support member 5 about the axis-of-rotation Ob. The electromagnetic lock 16c is provided on the arm 6d, and serves as fourth locking means capable of electrically locking the arm 6a about the axis-of-rotation Oc. The electromagnetic lock 16d is provided on the arm 6a, and serves as locking means capable of electrically locking the arm 11a about the axis-of-rotation Oh. The electromagnetic lock 16e is provided on the arm 11a, and serves as locking means capable of electrically locking the arm 11b about the axis-of-rotation Oi. The electromagnetic lock 16f is provided on the arm 11b, and serves as locking means capable of electrically locking the arm 11c about the axis-of-rotation Oj.

The arm (second arm) 6b of the first parallel link mechanism 6 has a balancing device. A screw shaft 20 is secured to the rear end of the arm 6. The screw shaft 20 has a counterweight 21 as a balancing weight screwed thereon. On the screw shaft 20, the counterweight 21 can move in an axial direction. The counterweight 21 is a balancing weight for offsetting the torque created around the axis-of-rotation Oc by the total weight of the link mechanism 11, the holding section 13 and the rigid scope 12, thereby keeping a balanced state. Further, the positions and the weights of the first parallel link mechanism 6, the link mechanism 11, the support arm 4 and the counterweight 21 are determined so as to offset the torque created around the axes-of-rotation Oa, Ob, Oh, Oi and Oj.

The arm 6d of the first parallel link mechanism 6 has a pressing lever 25 as second operation transmission means.

Referring then to FIG. 2, the structure of the pressing lever 25 will be described. FIG. 2 is a longitudinal sectional view of the arm 6d along the axis-of-rotation Og, when viewed in a direction indicated by arrow a in FIG. 1. As aforementioned, the arm 6d is inserted in a through hole 26 formed in the upper support member 5 and can rotate about the axis-of-rotation Og relative to the upper support member 5. An upper collar 7a and a lower collar 7b are provided on the upper and lower surfaces of the upper support member 5, respectively, thereby positioning the member 5 therebetween and enabling the member 5 to rotate without axially moving the arm 6d.

As shown in FIG. 2, the arm 6d has an axially-elongated hole 27 formed therein, a window 27a formed in an upper portion of a side wall of the arm and connected to the hole 27, and a window 27b that is formed in a lower portion of a side wall opposing the first-mentioned side and is closed by the inner surface of the upper support member 5, which defines part of the through hole 26. A pin 28 is provided in an intermediate position in the elongated whole 27 thereacross, and has opposite ends thereof secured to respective walls of the arm 6d. The pin 28 supports the pressing lever 25 such that the lever can rotate about the pin.

An input section (input operation section) 25a as second input means for pushing the pressing lever 25 into the hole 27 is attached to the upper end of the lever 25 outside the window 27a. A compressed spring 29, which pushes the pressing lever 25 in a direction opposite to the above pushing operation, is provided in the hole 27 between an upper portion of the side wall of the arm 6d opposed to the window 27a, and an upper portion of the pressing lever 25 remote from the input section 25a. The other end of the pressing lever 25 opposite to the input section 25a constitutes a pressing section 25b as third locking means. The pressing section 25b is situated at the lower window 27b and presses against the inner surface of the upper support member 5, which defines part of the through hole 26.

The compressed spring 29 urges the pressing lever 25 as shown in FIG. 2, whereby the pressing section 25b as the third locking means, which constitutes an end opposite to the input section 25a, is pushed against the upper support member 5 to thereby lock the arm 6d about the axis-of-rotation Og. In other words, the section 25b constitutes means for stopping the arm 6d rotating about the axis-of-rotation Og. When the input section 25a has been pushed to thereby rotate the pressing lever 25 and move the pressing section 25b away from the upper support member 5, the rotating-disabled state is released.

Referring to FIG. 3, an electric circuit incorporated in the medical instrument holding apparatus will be described. The release switch 17 as the first input means is electrically connected to a driving circuit 30 as first operation transmission means. The driving circuit 30 is electrically connected to the electromagnetic locks 16a, 16b, 16c, 16d, 16e and 16f. When the release switch 17 as the first input means has been turned on, the driving circuit 30 outputs a driving signal in response to a signal indicating the activation of the switch, thereby releasing the locking function of the locks 16a–16f.

A description will now be given of a case where an endoscope is moved during a surgical operation executed using the medical instrument holding apparatus according to the first embodiment. First, the medical instrument holding apparatus is attached to the side rail 3 of the surgical bed 2. Specifically, the installation table 1a is fitted on the side rail 3 and fastened to a portion of the rail appropriate for the operation by a fastening screw (not shown).

Subsequently, the rigid scope 12 held by the holding section 13 is moved to a to-be-operated area of a patient. At this time, the release switch 17 as the first input means is turned on, thereby inputting a signal to the driving circuit 30. The driving circuit 30, in turn, outputs a driving signal for releasing the locking function of the electromagnetic locks 16a–16f.

After releasing the locking function of the electromagnetic lock 16a as the first locking means, the support arm 4 is free to rotate about the axis-of-rotation Oa (first axis of rotation) relative to the support table 1b. Accordingly, the rigid scope 12 held by the holding section 13 is free to rotate about the axis-of-rotation Oa relative to the support table 1b, together with the first parallel link mechanism 6 and the link mechanism 11. When the locking function of the electromagnetic lock 16b as the second locking means has been released, the upper support member 5 is free to rotate about the axis-of-rotation Ob (second axis of rotation) relative to the support arm 4. Accordingly, the first parallel link mechanism 6 is free to rotate about the axis-of-rotation Ob. Therefore, the rigid scope 12 is also free to rotate about the axis-of-rotation Ob relative to the support arm 4, together with the link mechanism 11. Further, when the locking function of the electromagnetic lock 16c as the fourth locking means has been released, the arm 6a is free to rotate about the axis-of-rotation Oc relative to the arm 6b. Accordingly, the rigid scope 12 is free to rotate, to a large extent, about the axis-of-rotation Oc relative to the arm 6d, together with the link mechanism 11. The combination of rotating operations in three orthogonal directions enables the rigid scope 12 to move three-dimensionally.

On the other hand, when the electromagnetic lock 16d has been released, the arm 11a of the link mechanism 11 is free to rotate about the axis-of-rotation Oh relative to the arm 6a of the first parallel link mechanism 6. Further, when the electromagnetic lock 16e has been released, the arm 11b can rotate about the axis-of-rotation Oi relative to the arm 11a. Furthermore, when the electromagnetic lock 16f has been released, the arm 11c and the holding section 13 are free to rotate about the axis-of-rotation Oj relative to the arm 11c. In other words, the rigid scope 12 can execute nutational movements, i.e. three-dimensional movements about an intersection T between the axis-of-rotation Oh and the axis-of-rotation Oi. Thus, the rigid scope 12 can be three-dimensionally positioned with three degrees of freedom, and tilted about three orthogonal axes, i.e. tilted with three degrees of freedom.

A description will now be given of a method for fixing the arm 6d of the first parallel link mechanism 6 to the upper support member 5 such that the arm 6d does not rotate about the axis-of-rotation Og, a method for releasing the locked state of the arm 6d, and operations relating to the methods.

Figure 5:
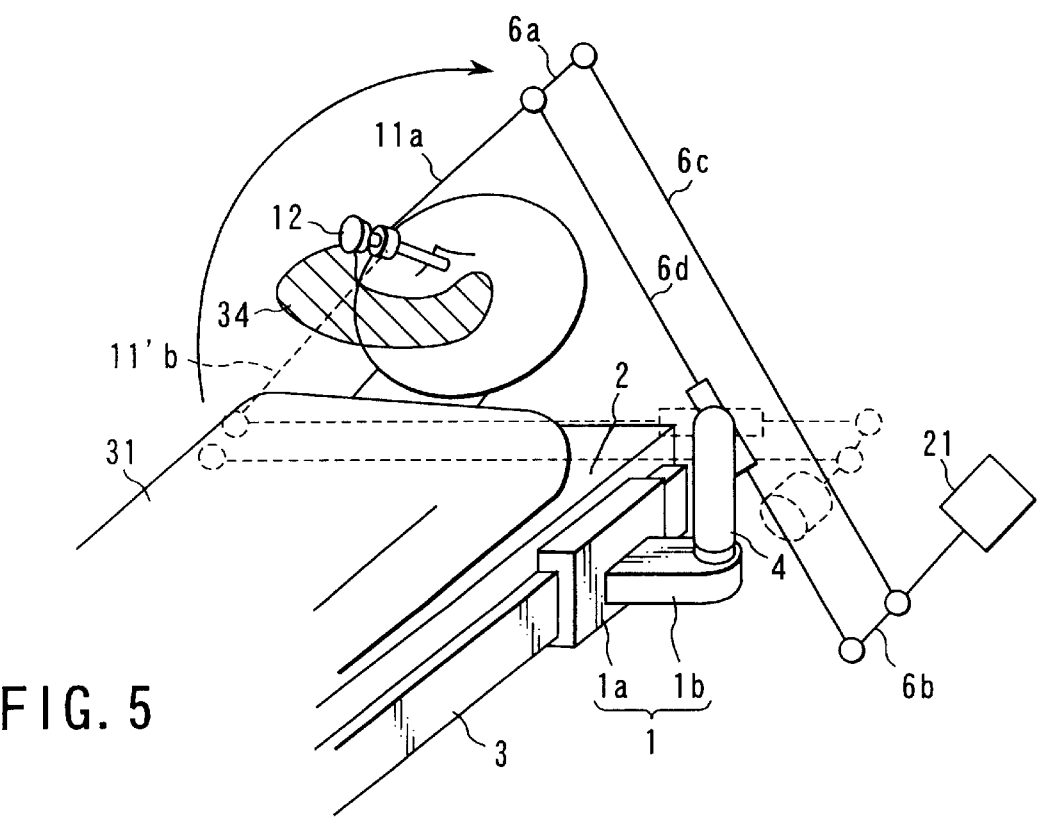
FIG. 5 is a view useful in explaining another state of the surgical operation using the medical instrument holding apparatus of the first embodiment.

FIGS. 4 and 5 illustrate states of a surgical operation using the medical instrument holding apparatus of the first embodiment. In this surgical operation, a to-be-operated portion 32 is located in a parietal region of a patient 31, and a surgical microscope 33 for magnifying the to-be-operated portion 32 is provided above the portion 32.

If the arms 6a–6d of the first parallel link mechanism 6 and the arm 11a of the link mechanism 11 are situated in positions 6a'–6d', and 11a' indicated by the broken lines in FIG. 4, the arms 6a–6d or the arm 11a interrupts the surgical microscope 33, thereby interrupting the observation of the to-be-operated portion 32.

In this case, the following operation is executed. While turning on the release switch 17 as the first input means, the input section 25a of the pressing lever 25, serving as the second input means, is pushed with the arm 6d gripped. As a result, the pressing lever 25 as the second operation transmission means rotates about the pin 28, thereby separating the pressing section 25b from the upper support member 5. In other words, the electromagnetic locks 6a–6f are released, and the arm 6d can rotate about the axis-of-rotation Og. As a result, the arms of the medical instrument holding apparatus can be moved with a further degree of freedom in addition to the aforementioned scope of movement.

Accordingly, the arms 6a–6d and 11a can be moved to respective positions as indicated by the solid lines in FIG. 4, in which they do not interrupt the surgical microscope 33, without changing the installation position of the installation table 1a of the medical instrument holding apparatus on the side rail 3 and the position of the front end of the rigid scope 12. In this state, the rigid scope 12 can be positioned three-dimensionally with three degrees of freedom, and tilted about three orthogonal axes, i.e. tilted with three degrees of freedom.

In the above case, the arms 6a–6d and 11a positioned above the patient are moved to the underside of the patient, thereby avoiding their interference with the surgical microscope 33. Their interference with the surgical microscope 33 can also be avoided by revolving the arms 6a–6d and 11a through 90° to make them horizontal.

FIG. 5 shows an example of a case where a surgical operation for approaching the pituitary gland of a patient 31 from the nose or its vicinities. In this case, the rigid scope 12 is inserted from the underside of the nose toward the pituitary gland. In order to secure a working space 34 in which the medical instrument is inserted, it is desirable that the arm 11a should be situated in the position indicated by the solid line in FIG. 4. When, in this case, the release switch 17 has been turned on and the pressing lever 25 has been pushed, the arm 11a can rotate about the axis-of-rotation Og, whereby it can be shifted from the position 11a' to the position indicated by the solid line and locked in the position, as in the previously described case.

Further, in this state, the rigid scope 12 can be moved three-dimensionally and tilted about each of the three orthogonal axes.

In the first embodiment, the parallel link mechanism 6 as balancing means enhances the rigidity of the second arm 6d, and also secures the balancing state between the medical instrument such as an endoscope and the counterweight.

The third locking means and the second operation transmission means (that also serves as the second input means) are mechanical elements and not electrical components. This means that no cable is necessary and hence they can be constructed easily and cost-effectively.

Since the axis-of-rotation Og (third axis of rotation) is made to be identical to the axis of the arm 6d (second arm), the upper support member 5 (first arm) that supports the arm 6d is prevented from projecting from the arm and has a simple structure.

Moreover, since the second input means is provided in the arm 6d (second arm) that can rotate when the second input means is operated, the arm 6d can be positioned while it is gripped. This means that the arm 6d can be positioned easily.

(Modification of the First Embodiment)

Figure 6:
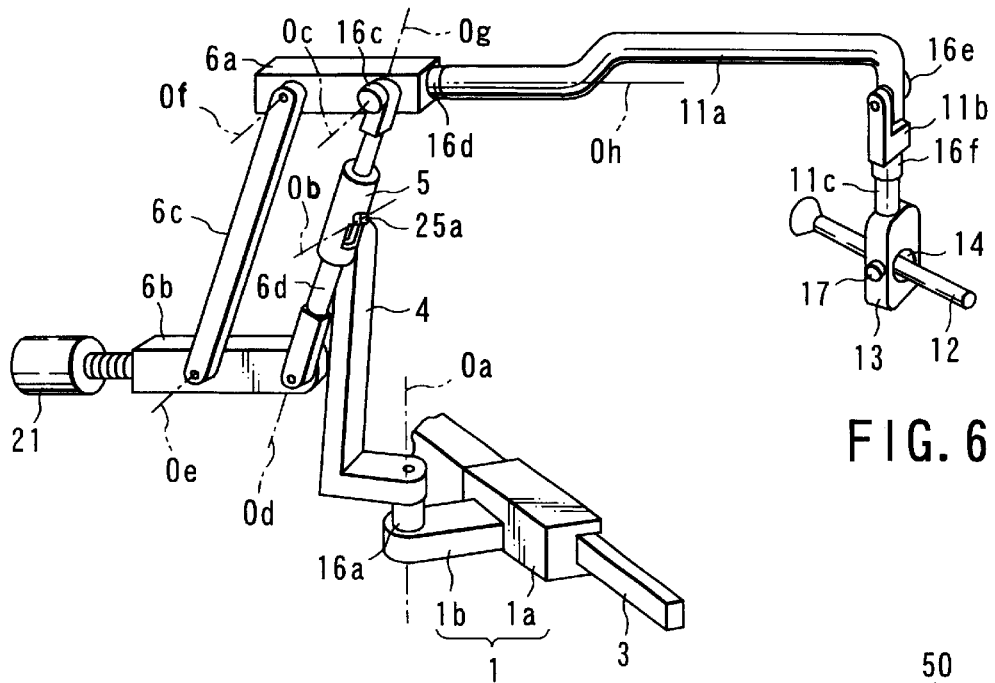
FIG. 6 is a schematic perspective view illustrating a medical instrument holding apparatus according to a modification of the first embodiment.

As shown in FIG. 6, in a holding apparatus according to a modification of the first embodiment, an input section 25a as second input means is provided in an upper support member 5 (first arm), and second locking means similar to the pressing lever 25 and rotatable about an axis-of-rotation Ob is provided. The movement of a rigid scope 12 about each of axes-of-rotation Oa, Og and Oc is disabled and enabled by operating a release switch 17 as first input means, and the movement of the mirror about the axis-of-rotation Ob is disabled and enabled by operating the input section 25a. This modification can provide the same advantage as that of the first embodiment.

(Second Embodiment)

Figure 7:
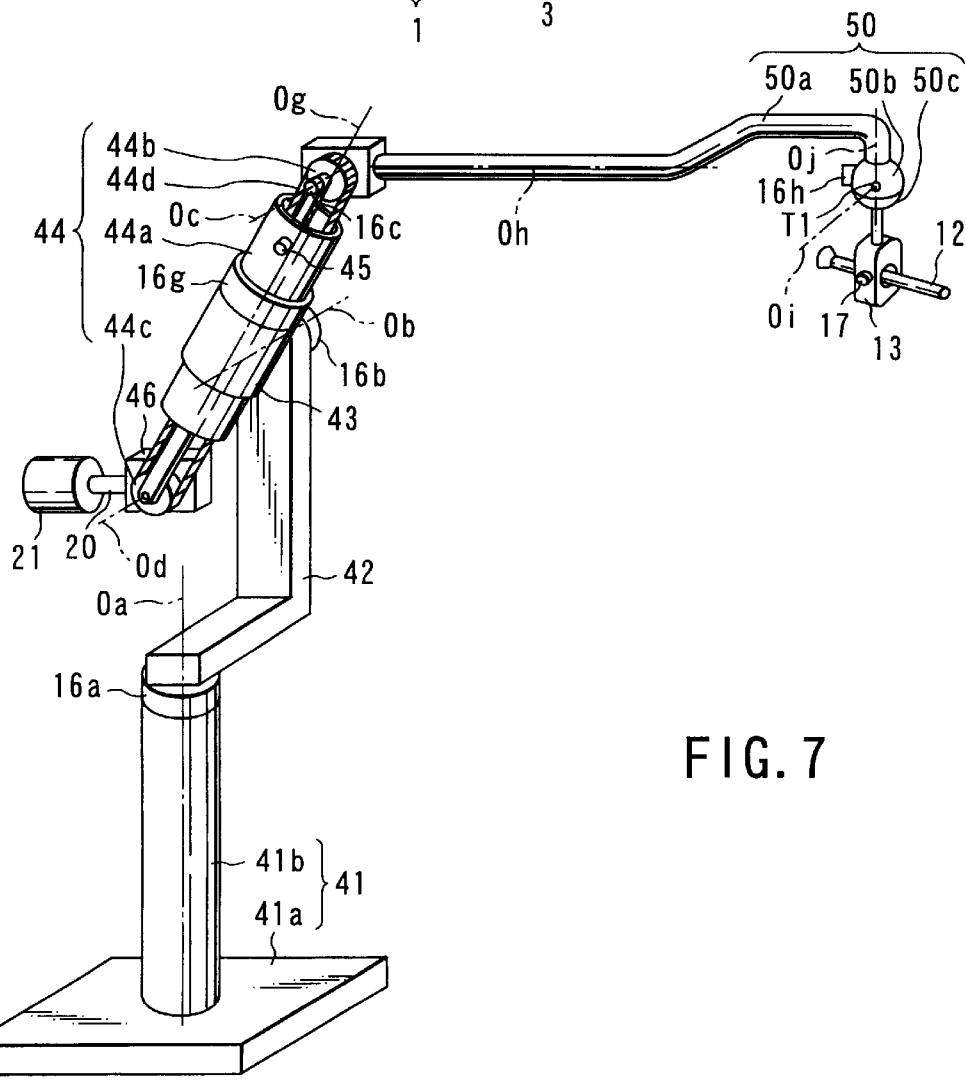
FIG. 7 is a schematic perspective view illustrating a medical instrument holding apparatus according to a second embodiment.
Figure 8:
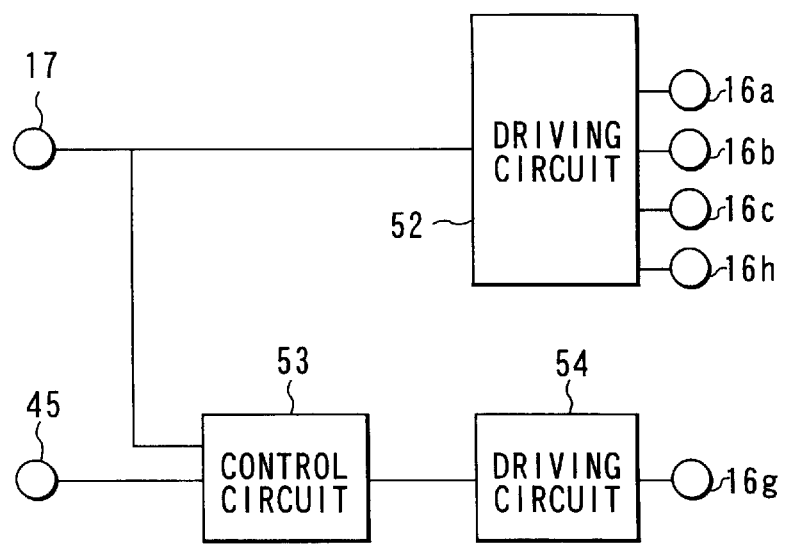
FIG. 8 is a view useful in explaining an electrical circuit incorporated in the medical instrument holding apparatus of the second embodiment.
Figure 9:
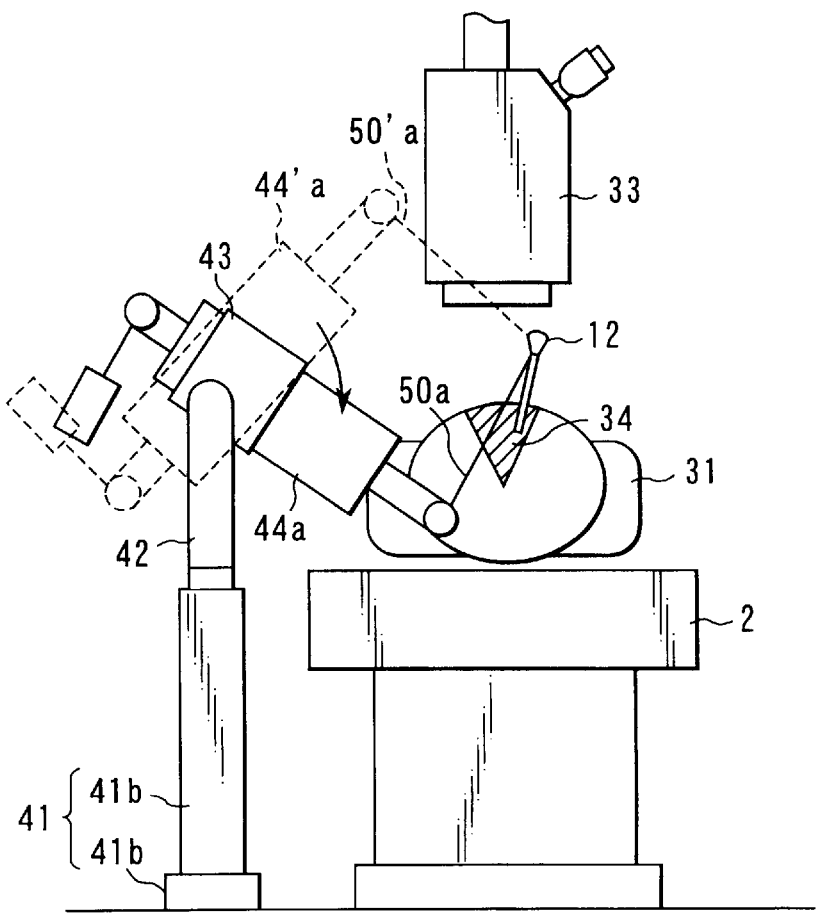
FIG. 9 is view useful in explaining a state of a surgical operation using the medical instrument holding apparatus of the second embodiment.

Referring then to FIGS. 7–9, a second embodiment of the invention will be described. In the second embodiment, reference numerals corresponding to those in the first embodiment denote similar elements, and no detailed description is given thereof.

FIG. 7 is a schematic perspective view illustrating a medical instrument holding apparatus according to a second embodiment. In FIG. 7, reference numeral 41 denotes an installation section of the holding apparatus. The installation section 41 comprises an installation table 41a that can be fixed to a surgical bed, and a support table 41b upwardly extending from the installation table 41a. A support arm 42 is connected to the upper end of the support table 41b such that the arm 42 can rotate about an axis-of-rotation Oa (first axis of rotation).

The upper end of the support arm 42 supports a support member 43 as a first arm such that the member 43 can rotate about an axis-of-rotation Ob (second axis of rotation), which extends perpendicular to the axis-of-rotation Oa. The support member 43 supports an arm 44 as a second arm such that the arm 44 can rotate about an axis-of-rotation Og (third axis of rotation), which extends perpendicular to the axis-of-rotation Ob and also to axes-of-rotation Oc and Od described later. The arm 44a has a second release switch 45 as second input means for operating an electromagnetic lock 16g as third locking means, which will be described later.

An axis-of-rotation Oc (fourth axis of rotation) and an axis-of-rotation Od parallel thereto are provided at the opposite ends of the arm 44a. A pulley 44b is provided at one end of the arm 44a such that it can rotate about the axis-of-rotation Oc. A pulley 44c is provided at the other end of the arm 44a such that it can rotate about the axis-of-rotation Od. The pulleys 44b and 44c have the same diameter. A belt 44d is wound on the pulleys 44b and 44c and connects them. The pulleys 44b and 44c are interlocked by the belt 44d such that they simultaneously rotate in the same direction at the same rotational speed. The arm 44a, the pulleys 44b and 44c and the belt 44d as a winding transmission member constitute a belt mechanism (winding means) 44.

A block 46 is attached to the pulley 44c. A screw shaft 20 is fixed to the block 46. A link mechanism 50 as a holding section tilting mechanism is connected to the pulley 44b. The link mechanism 50 comprises an arm 50a having one end thereof connected to the pulley 44b, and a ball-and-socket joint provided at the other end of the arm 50a, consisting of a socket section 50b and a ball section 50c received by the socket section 50b. The socket section 50b is provided at the distal end of the arm 50a along an axis-of-rotation Oj. The ball section 50c is supported by the socket section 50b such that the ball section 50c can tilt about a nutational point T1, and can rotate about an axis-of-rotation Oj.

An electromagnetic lock 16h, described later, is provided on the socket section 50b for stopping the tilting operation or the rotation of the ball section 50c. A holding section 13 for holding a rigid scope 12 is connected to the outside end of the ball section 50c. The rigid scope 12 can be attached to and detached from the holding section 13. Further, the holding section 13 includes a release switch 17 as first input means for operating electromagnetic locks 16a–16c and 16h as locking means described later.

The screw shaft 20 is fixed to the block 46 connected to the pulley 44c. A counterweight 21 as a balancing weight is axially movably mounted on the screw shaft 20. The counterweight 21 is a balancing weight for offsetting the torque created around the axis-of-rotation Oc by the total weight of the link mechanism 50 and the rigid scope 12, thereby keeping a balanced state.

Further, the positions and the weights of the belt mechanism 44, the support arm 42, the link mechanism 50 and the counterweight 21 are determined so as to offset the torque created around the axes-of-rotation Oa, Ob, Oh, Oi and Oj.

A description will be given of the electromagnetic locks 16a–16c, 16g and 16h as locking means. As shown in FIG. 7, the electromagnetic lock 16a as first locking means is provided on the support table 41b for electrically stopping the rotating operation of the support arm 42 about the axis-of-rotation Oa relative to the support table 41b. The electromagnetic lock 16b as second locking means is provided on an upper end portion of the support arm 42 for electrically stopping the rotating operation of the support member 43 about the axis-of-rotation Ob. The electromagnetic lock 16c as fourth locking means is provided on the arm 44a for electrically stopping the rotation of the pulley 44b and the rotating operation of the arm 50a about the axis-of-rotation Oc. The electromagnetic lock 16h is provided on the socket section 50b for electrically stopping the tilting operation of the ball section 50c about the nutational point T1 and the rotation of the ball section 50c about the axis-of-rotation Oj. The electromagnetic lock 16g as third locking means is provided on the support member 42 for electrically stopping the rotation of the arm 44a about the axis-of-rotation Og.

Referring then to FIG. 8, the electric circuit incorporated in this embodiment will be described. The release switch 17 as the first input means is electrically connected to a driving circuit 52 as first operation transmission means. The driving circuit 52 is electrically connected to the electromagnetic locks 16a–16c and 16h. The release switch 17 as the first input means and the second release switch 45 are electrically connected to a control circuit 53, which is electrically connected to a driving circuit 54. The driving circuit 54 is further electrically connected to the electromagnetic lock 16g. The control means in this embodiment is constituted of the control circuit 53 and the driving circuit 54.

A description will be given of the movement of an endoscope, during a surgical operation, held by the medical instrument holding apparatus of the second embodiment. First, the medical instrument holding apparatus is moved to a portion of a surgical bed, which is appropriate to a surgical operation, and the installation table 41a of the apparatus is fixed on the appropriate portion of the bed.

Subsequently, when the rigid scope (endoscope) 12 is shifted to a to-be-operated portion of a patient, the release switch 17 is turned on. Then, a signal is input to the driving circuit 52, which, in turn, outputs a driving signal to release the locking function of the electromagnetic locks 16a, 16b, 16c and 16h.

After the locking function of the electromagnetic lock 16a is released, the support arm 42 is free to rotate about the vertical axis-of-rotation Oa. Accordingly, the rigid scope 12 is free to rotate about the vertical axis-of-rotation Oa relative to the installation section 41, together with the bent mechanism 44 and the link mechanism 50.

After the electromagnetic lock 16b is released, the support member 43 can rotate about the axis-of-rotation Ob relative to the support arm 42. Accordingly, the belt mechanism 44 can rotate about the axis-of-rotation Ob, and the rigid scope 12 is free to rotate about the axis-of-rotation Ob relative to the support arm 42, together with the link mechanism 50.

After the electromagnetic lock 16c is released, the pulley 44b and the arm 44a are free to rotate about the axis-of-rotation Oc. Accordingly, the rigid scope 12 can to rotate about the axis-of-rotation Oc relative to the arm 44a, together with the link mechanism 50. Thus, the combination of rotating operations in three directions enables the rigid scope 12 held by the holding apparatus to be moved three-dimensionally.

After the electromagnetic lock 16h is released, the ball section 50c is free to tilt about the nutational point T1 and to rotate about the axis-of-rotation Oj relative to the socket section (arm) 50b. Accordingly, at this time, the rigid scope 12 can tilt about the mutational point T1 and rotate about the axis-of-rotation Oj relative to the arm 50a.

In other words, the operation of the locking means can be selected so as to position the rigid scope 12 with three degrees of freedom, or to tilt or rotate it about the nutational point Ti with three degrees of freedom.

A description will now be given of a method for disabling and enabling the rotation of the arm 44a about the axis-of-rotation Og relative to the support member 43, and also of operations relating to the rotation.

FIG. 9 shows a state of a surgical operation using the medical instrument holding apparatus of the second embodiment. In this surgical operation, a to-be-operated portion 34 is located in a parietal region of a patient 31, and a surgical microscope 33 for magnifying the to-be-operated portion 32 is provided above the portion 32. If the arms 44a and 50a of the holding apparatus are situated in positions 44a'–50a' indicated by the broken lines in FIG. 9, the arms 44a and 50a interrupt the surgical microscope 33, thereby interrupting the observation of the to-be-operated portion 34.

In this case, while turning on the release switch 17, the second release switch 45 is turned on. As a result, the electromagnetic locks 16a–16c and 16h are released, and at the same time, the control circuit 53 outputs a signal in response to signals generated from the second release switch 45 and the release switch 17, thereby controlling the driving circuit 54 so as to release the electromagnetic lock 16g. Accordingly, the arm 44a can rotate about the axis-of-rotation Og. In other words, the arms of the holding apparatus can be moved with a further degree of freedom in addition to the aforementioned scope of movement. Therefore, the operation of the locking means can be selected so as to move the arms 44a and 50a to positions 44a and 50a indicated by the solid lines in FIG. 9, in which they do not interrupt the surgical microscope 33, without changing the installation position of the installation table 41a on the surgical bed and the position of the front end of the rigid scope 12. In this state, the rigid scope 12 can be moved to a desired location.

If, in this state, the release switch 17 is turned on, the rigid scope 12 can be three-dimensionally positioned with three degrees of freedom, and tilted and rotated with three degrees of freedom about the nutational point T1.

In the above case, the arms 44a and 50a positioned above the patient are moved to the underside of the patient, thereby avoiding their interference with the surgical microscope 33, as in the first embodiment. Their interference with the surgical microscope 33 can also be avoided by revolving the arms through 90° to make them horizontal.

Further, since the control circuit 53 outputs a signal to the driving circuit 54 only when it has simultaneously received signals from the second release switch 45 and the release switch 17, the electromagnetic lock 16g is not released even if only the second release switch 45 is erroneously turned on.

The second embodiment, which employs a belt mechanism as winding transmission mechanism in place of the parallel movement means, can provide the same advantage as the first embodiment. Further, the second embodiment is more advantageous than the first embodiment in that the former can be constructed by a smaller number of component parts than the latter. Moreover, the control circuit 53 as control means enables the electromagnetic lock 16g to be kept locked even when the second release switch 45 is erroneously pushed. This means that the operator can operate the arm 44a only when they intend to do so, and hence can concentrate on the surgical operation itself.

The same advantage as above can be obtained even when the belt 44d as the winding transmission member is replaced with a chain.

(Third Embodiment)

Referring to FIGS. 10–15, a third embodiment of the invention will be described. In the third embodiment, reference numerals corresponding to those in the first embodiment denote similar elements, and no detailed description is given thereof.

Figure 10:
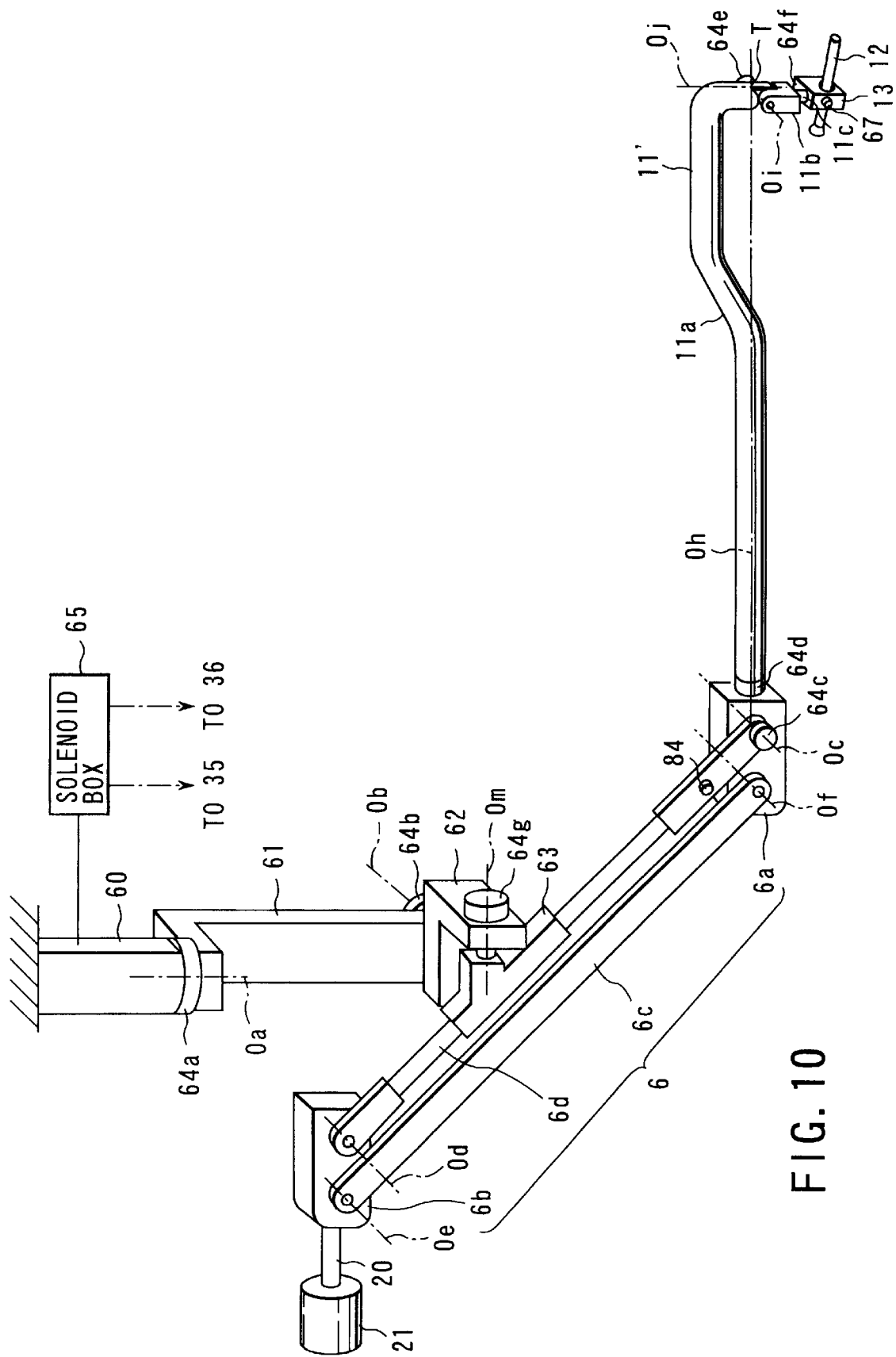
FIG. 10 is a schematic perspective view illustrating a medical instrument holding apparatus according to a third embodiment.

FIG. 10 is a schematic perspective view illustrating a medical instrument holding apparatus according to the third embodiment. In FIG. 10, reference numeral 60 denotes an installation section fixed on the ceiling of an operation room. A support arm 61 is connected to the lower end of the installation section 60 such that the arm can rotate eccentrically about an axis-of-rotation Oa (first axis of rotation). A rotating block 62 as a first arm is connected to the lower end of the support arm 61 such that the block can rotate about an axis-of-rotation Ob (second axis of rotation) perpendicular to the axis-of-rotation Oa. The rotating block 62 supports a support member 63 as a second arm such that the member 63 can rotate about a substantially horizontal axis-of-rotation Om (third axis of rotation) perpendicular to the axis-of-rotation Ob. A solenoid box 65 described later is connected to the installation section 60.

A first parallel link mechanism 6 having the same structure as that in the first embodiment is connected to the rotating block 62. The first parallel link mechanism 6 includes four arms 6a, 6b, 6c and 6d that form a parallelogram. The arms 6a and 6b are maintained in a parallel relationship to each other by the arms 6c and 6d, which can rotate about axes-of-rotation Oe, Of, Oc and Od, respectively.

The support member 63 is mounted on the arm 6d. The arm 6d has a second release switch 84 for operating a spring-tensioned locking mechanism 64g as third locking means described later.

A screw shaft 20 is fixed to the arm 6b of the first parallel link mechanism 6, and a counterweight 21 as a balancing weight is axially movably mounted on the shaft 20, as in the first embodiment. The counterweight 21 is a balancing weight for offsetting the torque created around the axis-of-rotation Oc by the total weight of a link mechanism 11n and a rigid scope 12, thereby keeping a balanced state. The counterweight 21 constitutes a balancing unit. The positions and the weights of the first parallel link mechanism 6, the link mechanism 11, the support arm 61 and the counterweight 21 are determined so as to offset the torque created around the axes-of-rotation Oa, Ob, Oh, Oi and Oj.

The link mechanism 11 is holding section tilting means having the same structure as in the first embodiment, and includes arms 11a, 11b and 11c. The arm 11c is connected to a holding section 13 for holding the rigid scope 12. A release switch 67 as first input means is provided on the holding section 13 for operating spring-tensioned locking mechanisms 64a–64f as locking means.

The spring-tensioned locking mechanisms 64a–64g as locking means will be described. As illustrated in FIG. 10, the locking mechanism 64a as first locking means is provided on the installation section 60 for stopping the support arm 61 rotating about the axis-of-rotation Oa relative to the installation section 60. The locking mechanism 64b as second locking means is provided on a lower portion of the support arm 61 for stopping the rotating block 62 rotating about the axis-of-rotation Ob. The locking mechanism 64c as fourth locking means is provided on the arm 6d for stopping the arm 6a rotating about the axis-of-rotation Oc. The locking mechanism 64d is provided on the arm 11a for stopping the arm 11a rotating about the axis-of-rotation Oh. The locking mechanism 64e is provided on the arm 11a for stopping the arm 11b rotating about the axis-of-rotation Oi. The locking mechanism 64f is provided on the arm 11b for stopping the arm 11c rotating about the axis-of-rotation Oj. The locking mechanism 64g as third locking means is provided on the rotating block 62 for stopping the support member 63 rotating about the axis-of-rotation Om.

Referring to FIG. 11, the spring-tensioned locking mechanisms 64a–64g, the solenoid box 65 and its electric circuit will be described. Concerning the locking mechanisms, only the locking mechanism 64f will be described since they have similar structures.

As shown in FIG. 11, a shaft 71 as a support shaft is supported by the arm 11b such that the shaft can rotate about the axis-of-rotation Oj, and is also fixed to the arm 11c. A cylinder 72 is provided on the arm 11c. Fixing elements 74a and 74b, a support shaft 75b and a first fixing member 80a are secured to the cylinder 72. Two coiled springs 78a and 78b as elastic members, which have a smaller diameter than the shaft 71 in a natural state, are wound on the shaft 71. Therefore, when the two coiled springs 78a and 78b are mounted on the shaft 71, they generate fastening forces acting toward the center of the shaft 71. The springs 78a and 78b are coiled in opposite directions. Further, the springs 78a and 78b have one of their respective ends secured to the cylinder 72 by means of their respective fixing elements 74a and 74b, and the other ends kept in contact with a rotatable block 75a.

The rotatable block 75a is supported by the support shaft 75b such that the block can rotate about an axis-of-rotation On. The support shaft 75b is secured to the cylinder 72. The rotatable block 75a is connected to one end of a wire 76f, which is connected to a solenoid 79f through an outer tube 77. The outer tube has one end thereof secured to the first fixing member 80a, and the other end thereof secured to a second fixing member 80b that is fixed to the solenoid box 65. The solenoid 79f is electrically connected to a driving circuit 81 as first operation transmission means.

The other spring-tensioned locking mechanisms 64a–64e have the same structure as the above, and solenoids 79a–79e connected thereto are also connected to the driving circuit 81.

A solenoid 79g connected to the spring-tensioned locking mechanism 64g is electrically connected to a driving circuit 82. The driving circuit 81 is electrically connected to the release switch 67. Further, the driving circuit 82 is electrically connected to a control circuit 83, which is electrically connected to the release switch 67 and a second release switch 84. In this embodiment, the control circuit 83 and the driving circuit 82 constitute control means.

A description will be given of how to release the locking function of the spring-tensioned locking mechanisms employed in the medical instrument holding apparatus of the third embodiment. First, the release switch 67 is turned on to move the rigid scope 12 to a to-be-operated portion of a patient, thereby inputting a signal to the driving circuit 81. The driving circuit 81, in turn, outputs a driving signal to the solenoid 79f. The solenoid 79f pulls the wire 76f in a direction indicated by arrow 85 in FIG. 11. As a result, the rotatable block 75a rotates from a position indicated by the solid line to a position 75a' indicated by the broken line in FIG. 12. Accordingly, the free ends of the coiled springs 78a and 78b are shifted to positions 78a' and 78b' indicated by the broken lines in FIG. 12, respectively.

FIG. 12 shows the rotatable block 75a viewed in a direction indicated by arrow b in FIG. 11. A deformed state of the coiled spring 78a will be described with reference to FIG. 13. In accordance with the rotating movement of the rotatable block 75a, the coiled spring 78a is deformed such that its free end is shifted to the position 78a' indicated by the broken line. At this time, the inner diameter R of the coiled spring 78a is increased to R'. Since the inner diameter R' is larger than the diameter of the shaft 71, the shaft 71 is free to rotate relative to the cylinder 72. The cylinder 72 is fixed to the arm 11b, while the shaft 71 is fixed to the arm 11c. Accordingly, the locking function of the spring-tensioned locking mechanism 64f is released, thereby enabling the arms 11c to rotate about the axis-of-rotation Oj relative to the arm 11b.

Similarly, the locking functions of the spring-tensioned locking mechanisms 64a–64e can be released by turning on the release switch 67.

The release of the locking functions of the spring-tensioned locking mechanisms 64a–64f enables the rigid scope 12 to be three-dimensionally positioned with three degrees of freedom, and also to be tilted with three degrees of freedom, i.e. tilted about three orthogonal axes.

A description will be given of a method for stopping the support member 63 rotating about the axis-of-rotation Om relative to the rotatable block 62, and releasing the locking state.

FIG. 14 shows a state of a surgical operation using the medical instrument holding apparatus of the third embodiment. In this surgical operation, a to-be-operated portion 32 is located in a parietal region of a patient 31, and a surgical microscope 33 for magnifying the to-be-operated portion 32 is provided above the portion 32. If the arms 6a–6d and the arm 11a are situated in positions 6a'–6d' and 11a' indicated by the broken lines in FIG. 14, the arms 6a–6d and the arm 11a interrupt the surgical microscope 33, thereby interrupting the observation of the to-be-operated portion 32.

In this case, the following operation is executed. While turning on the release switch 67, the second release switch 84 is turned on. As a result, the electromagnetic locks 6a–6f are released, and at the same time, the control circuit 83 outputs a signal to the driving circuit 82 in response to signals from the release switches 67 and 84, thereby releasing the locking function of the spring-tensioned locking mechanism 64g. Accordingly, the arm 6d is free to rotate about the axis-of-rotation Om. Thus, as in the first embodiment, the arms of the holding apparatus can be moved with a further degree of freedom in addition to the aforementioned scope of movement. Therefore, the arms 6a–6d and 11a can be shifted to and kept in the positions 6a–6d and 11a indicated by the solid lines in FIG. 14, in which the arms do not interrupt the surgical microscope 33, without changing the installation position of the installation section 60 on the ceiling of the operation room, and also without changing the position of the front end of the rigid scope 12.

At this time, the arms 6a–6d and 11a can be moved simply by rotating the support member 63 about the axis-of-rotation Om, without having to perform a lengthy combined maneuver of rotating the support arm 61 or the rotatable block 62 about the axis-of-rotation Oa or Ob.

Moreover, in this state, if the release switch 67 is turned on, the rigid scope 12 can be three-dimensionally positioned with three degrees of freedom, and also tilted with three degrees of freedom, i.e. tilted about three orthogonal axes.

In the above case, the arms 6a–6d and 11a positioned above the patient are moved to the underside of the patient, thereby avoiding their interference with the surgical microscope 33. Their interference with the surgical microscope 33 can also be avoided by revolving the arms 6a–6d and 11a through 90° to make them horizontal.

Further, since the control circuit 83 outputs a signal to the driving circuit 82 only when it has simultaneously received signals from the release switch 67 and the second release switch 84, the spring-tensioned locking mechanism 64g is not released even if only the second release switch 84 is turned on.

The third embodiment can provide the same advantage as the first embodiment even if the axis-of-rotation Om (third axis of rotation) is situated in a direction different from that of the first embodiment. Furthermore, in the third embodiment, when making the axis-of-rotation Om substantially horizontal to avoid the interference between the surgical microscope and the medical instrument, the arms 6a–6d and 11a can be moved simply by rotating the support member 63 about the axis-of-rotation Om, without rotating, to a large extent, the support arm 61 or the rotatable block 62 about the axis-of-rotation Oa or Ob. Thus, the interference between them can be easily avoided.

The coiled springs 78a and 78b may be replaced with a plate spring 90 as shown in FIG. 15. Also in this case, the same advantage can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical instrument holding apparatus comprising:
an installation section to be supported by a member in an operation room;
a support arm supported by the installation section such that the support arm is rotatable about a first axis of rotation;
a first arm supported by the support arm such that the first arm is rotatable about a second axis of rotation perpendicular to the first axis of rotation;
a second arm supported by the first arm such that the second arm is rotatable about a third axis of rotation perpendicular to the second axis of rotation;
a third arm supported by the second arm such that the third arm is rotatable about a fourth axis of rotation perpendicular to the third axis of rotation;
a holding section tilting/rotating mechanism supported by a front end portion of the third arm;
a medical instrument holding section supported by the holding section tilting/rotating mechanism such that the medical instrument holding section is tiltable and rotatable, the medical instrument holding section being designed to hold a medical instrument;
first, second, third and fourth locking units for locking the support arm, the first arm, the second arm and the third arm about the first axis of rotation, the second axis of rotation, the third axis of rotation and the fourth axis of rotation, respectively, and for releasing a locked state of the support arm, the first arm, the second arm and the third arm; and
a control unit capable of controlling a selected one of the first, second, third and fourth locking units.

2. The medical instrument holding apparatus according to claim 1, wherein the control unit has an operation switching unit for switching an operation of the control unit between control for causing predetermined three of the first, second, third and fourth locking units to execute a locking operation, and control for causing all the first, second, third and fourth locking units to execute a locking operation.

3. The medical instrument holding apparatus according to claim 2, wherein the second arm has a balancing unit for offsetting a torque created around the first, second, third and fourth axes.

4. The medical instrument holding apparatus according to claim 3, wherein the operation switching unit includes a first operation transmission unit responsive to information supplied from a first input unit for simultaneously causing the first, second and fourth locking units to execute the locking operation, and a second operation transmission unit responsive to information supplied from a second input unit for causing the third locking unit to execute the locking operation.

5. The medical instrument holding apparatus according to claim 4, wherein the first input unit is provided on the medical instrument holding section, and the second input unit is provided on the second arm.

6. The medical instrument holding apparatus according to claim 3, wherein the operation switching unit includes a first operation transmission unit responsive to information supplied from a first input unit for simultaneously causing the first, second and fourth locking units to execute the locking operation, and a second operation transmission unit responsive to information supplied from a second input unit for causing the second locking unit to execute the locking operation.

7. The medical instrument holding apparatus according to claim 6, wherein the first input unit is provided on the medical instrument holding section, and the second input unit is provided on the first arm.

8. The medical instrument holding apparatus according to claim 3, wherein the operation switching unit includes a first operation transmission unit responsive to information supplied from a first input unit for simultaneously causing the first, second and fourth locking units to execute the locking operation, a second input unit, and a second operation transmission unit responsive to information supplied from the second input unit for causing the third locking unit to execute the locking operation.

9. The medical instrument holding apparatus according to claim 8, wherein the first input unit is provided on the medical instrument holding section, and the second input unit is provided on the second arm.

10. The medical instrument holding apparatus according to claim 3, wherein the operation switching unit includes a first operation transmission unit responsive to information supplied from a first input unit for simultaneously causing the first, third and fourth locking units to execute the locking operation, a second input unit, and a second operation transmission unit responsive to information supplied from the second input unit for causing the second locking unit to execute the locking operation.

11. The medical instrument holding apparatus according to claim 10, wherein the first input unit is provided on the medical instrument holding section, and the second input unit is provided on the first arm.

12. The medical instrument holding apparatus according to claim 2, wherein the operation switching unit includes a first operation transmission unit responsive to information supplied from a first input unit for simultaneously causing the first, second and fourth locking units to execute the locking operation, and a second operation transmission unit responsive to information supplied from a second input unit for causing the third locking unit to execute the locking operation.

13. The medical instrument holding apparatus according to claim 12, wherein the first input unit is provided on the medical instrument holding section, and the second input unit is provided on the second arm.

14. The medical instrument holding apparatus according to claim 2, wherein the operation switching unit includes a first operation transmission unit responsive to information supplied from a first input unit for simultaneously causing the first, second and fourth locking units to execute the locking operation, and a second operation transmission unit responsive to information supplied from a second input unit for causing the second locking unit to execute the locking operation.

15. The medical instrument holding apparatus according to claim 14, wherein the first input unit is provided on the medical instrument holding section, and the second input unit is provided on the first arm.

16. The medical instrument holding apparatus according to claim 2, wherein the operation switching unit includes a first operation transmission unit responsive to information supplied from a first input unit for simultaneously causing the first, second and fourth locking units to execute the locking operation, a second input unit, and a second operation transmission unit responsive to information supplied from the second input unit for causing the third locking unit to execute the locking operation.

17. The medical instrument holding apparatus according to claim 16, wherein the first input unit is provided on the medical instrument holding section, and the second input unit is provided on the second arm.

18. The medical instrument holding apparatus according to claim 2, wherein the operation switching unit includes a first operation transmission unit responsive to information supplied from a first input unit for simultaneously causing the first, third and fourth locking units to execute the locking operation, a second input unit, and a second operation transmission unit responsive to information supplied from the second input unit for causing the second locking unit to execute the locking operation.

19. The medical instrument holding apparatus according to claim 18, wherein the first input unit is provided on the medical instrument holding section, and the second input unit is provided on the first arm.

20. The medical instrument holding apparatus according to claim 1, wherein the second arm has a balancing unit for offsetting a torque created around the first, second, third and fourth axes.

21. A medical instrument holding apparatus comprising:
an arm unit including a plurality of arm members supported such that the arm members are rotatable about their respective axes of rotation;
a locking unit for locking a pair of adjacent ones of the arm members of the arm unit about their respective axes, and for releasing a locked state of the pair of arm members, the locking unit having a support shaft arranged coaxially with a corresponding one of the axes, an elastic member provided at an outer periphery of the support shaft, and a deforming unit for deforming and enlarging a diameter of the elastic member, the elastic member being in contact with the outer periphery of the support shaft when the pair of arm members are locked, and out of contact therewith when the pair of arm members are released, the diameter of the elastic member being smaller than an outer diameter of the support shaft when the elastic member is in a natural state; and
a medical instrument holding section supported by one of the arm members for holding a medical instrument.

* * * * *